United States Patent
Altshuler et al.

(10) Patent No.: US 6,663,620 B2
(45) Date of Patent: *Dec. 16, 2003

(54) LIGHT ENERGY DELIVERY HEAD

(75) Inventors: Gregory B. Altshuler, Wilmington, MA (US); Henry M. Zenzie, Dover, MA (US)

(73) Assignee: Palomar Medical Technologies, Inc., Burlington, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 10/052,474

(22) Filed: Jan. 18, 2002

(65) Prior Publication Data

US 2002/0128635 A1 Sep. 12, 2002

Related U.S. Application Data

(63) Continuation of application No. 09/473,910, filed on Dec. 28, 1999, now Pat. No. 6,517,532, which is a continuation-in-part of application No. 09/078,055, filed on May 13, 1998, now Pat. No. 6,273,884.

(60) Provisional application No. 60/115,447, filed on Jan. 8, 1999, provisional application No. 60/164,492, filed on Nov. 9, 1999, provisional application No. 60/046,542, filed on May 15, 1997, and provisional application No. 60/077,726, filed on Mar. 12, 1998.

(51) Int. Cl.[7] .............................................. A61B 18/18

(52) U.S. Cl. ............................... 606/9; 606/613; 607/88

(58) Field of Search ................... 606/2–6, 9–12, 606/13, 14–18, 19; 607/89, 90, 91; 257/99

(56) References Cited

U.S. PATENT DOCUMENTS

| | | |
|---|---|---|
| 3,327,712 A | 6/1967 | Kaufman |
| 3,527,932 A | 9/1970 | Thomas |

(List continued on next page.)

FOREIGN PATENT DOCUMENTS

| | | |
|---|---|---|
| AT | 400 305 B | 4/1995 |
| DE | 3837248 A | 5/1990 |

(List continued on next page.)

OTHER PUBLICATIONS

Altshuler, Grigory B., et al., "Acoustic response of hard dental tissues to pulsed laser action," *SPIE*, vol. 2080, Dental Applications of Lasers (1993), pp. 97–103.

Altshuler, G. B., et al., "Extended Theory of Selective Photothermolysis," *Lasers in Surgery and Medicine*, 29:416–432 (2001).

(List continued on next page.)

*Primary Examiner*—Roy D. Gibson
(74) *Attorney, Agent, or Firm*—Thomas J. Engellenner; Deborah A. Miller; Nutter McClennen & Fish LLP

(57) ABSTRACT

A light energy delivery head is provided which, in one aspect, mounts laser diode bars or other light energy emitters in a heat sink block which is adapted to cool both the emitters and a surface of a medium with which the head is in contact and to which it is applying light energy. In another aspect, various retroreflection configurations are provided which optimize retroreflection of back-scattered light energy from the medium. The size of the aperture through which light energy is applied to the medium is also controlled so as to provide a desired amplification coefficient as a result of retroreflection.

20 Claims, 11 Drawing Sheets

U.S. PATENT DOCUMENTS

| | | |
|---|---|---|
| 3,538,919 A | 11/1970 | Meyer |
| 3,622,743 A | 11/1971 | Muncheryan |
| 3,693,623 A | 9/1972 | Harte et al. |
| 3,818,914 A | 6/1974 | Bender |
| 3,834,391 A | 9/1974 | Block |
| 3,900,034 A | 8/1975 | Katz et al. |
| 4,233,493 A | 11/1980 | Nath |
| 4,273,109 A | 6/1981 | Enderby |
| 4,316,467 A | 2/1982 | Muckerheide |
| 4,388,924 A | 6/1983 | Weissman et al. |
| 4,461,294 A | 7/1984 | Baron |
| 4,539,987 A | 9/1985 | Nath et al. |
| 4,608,978 A | 9/1986 | Rohr |
| 4,617,926 A | 10/1986 | Sutton |
| 4,695,697 A | 9/1987 | Kosa |
| 4,718,416 A | 1/1988 | Nanaumi |
| 4,733,660 A | 3/1988 | Itzkan |
| 4,747,660 A | 5/1988 | Nishioka |
| 4,819,669 A | 4/1989 | Politzer |
| 4,832,024 A | 5/1989 | Boussignac |
| 4,860,172 A | 8/1989 | Schlager et al. |
| 4,860,744 A | 8/1989 | Johnson et al. |
| 4,917,084 A | 4/1990 | Sinofsky |
| 4,926,227 A | 5/1990 | Jensen |
| 4,945,239 A | 7/1990 | Wist et al. |
| 5,000,752 A | 3/1991 | Hoskin et al. |
| 5,057,104 A | 10/1991 | Chess |
| 5,059,192 A | 10/1991 | Zaias |
| 5,065,515 A | 11/1991 | Iderosa |
| 5,071,417 A | 12/1991 | Sinofsky |
| 5,108,388 A | 4/1992 | Trokel |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,225,926 A | 7/1993 | Cuomo et al. |
| 5,226,907 A | 7/1993 | Tankovich |
| 5,282,797 A | 2/1994 | Chess |
| 5,300,097 A | 4/1994 | Lerner et al. |
| 5,304,170 A | 4/1994 | Green |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,344,418 A | 9/1994 | Ghaffari |
| 5,348,551 A | 9/1994 | Spears et al. |
| 5,350,376 A | 9/1994 | Brown |
| 5,380,317 A | 1/1995 | Everett et al. |
| 5,403,306 A | 4/1995 | Edwards et al. |
| 5,405,368 A | 4/1995 | Eckhouse |
| 5,415,654 A | 5/1995 | Daikuzono |
| 5,425,728 A | 6/1995 | Tankovich |
| 5,474,549 A | 12/1995 | Ortiz et al. |
| 5,486,172 A | 1/1996 | Chess |
| 5,505,726 A | 4/1996 | Meserol |
| 5,505,727 A | 4/1996 | Keller |
| 5,519,534 A | 5/1996 | Smith et al. |
| 5,578,866 A | 11/1996 | DePoorter et al. |
| 5,595,568 A | 1/1997 | Anderson et al. |
| 5,611,475 A | 3/1997 | Sim |
| 5,616,140 A | 4/1997 | Prescott |
| 5,620,478 A | 4/1997 | Eckhouse |
| 5,626,631 A | 5/1997 | Eckhouse |
| 5,630,811 A | 5/1997 | Miller |
| 5,649,972 A | 7/1997 | Hochstein |
| 5,655,547 A | 8/1997 | Karni |
| 5,662,643 A | 9/1997 | Kung et al. |
| 5,662,644 A | 9/1997 | Swor |
| 5,683,380 A | 11/1997 | Eckhouse |
| 5,698,866 A | 12/1997 | Doiron et al. |
| 5,735,844 A | 4/1998 | Anderson et al. |
| 5,735,884 A | 4/1998 | Thompson et al. |
| 5,743,901 A | 4/1998 | Grove et al. |
| 5,755,751 A | 5/1998 | Eckhouse |
| 5,759,200 A | 6/1998 | Azar |
| 5,782,249 A | 7/1998 | Weber et al. |
| 5,810,801 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,828,803 A | 10/1998 | Eckhouse |
| 5,830,208 A | 11/1998 | Muller |
| 5,836,999 A | 11/1998 | Eckhouse et al. |
| 5,849,029 A | 12/1998 | Eckhouse et al. |
| 5,853,407 A | 12/1998 | Miller |
| 5,885,211 A | 3/1999 | Eppstein et al. |
| 5,885,273 A | 3/1999 | Eckhouse et al. |
| 5,885,274 A | 3/1999 | Fullmer et al. |
| 5,944,748 A | 8/1999 | Mager et al. |
| 5,948,011 A | 9/1999 | Knowlton |
| 5,954,710 A | 9/1999 | Paolini et al. |
| 5,964,749 A | 10/1999 | Eckhouse et al. |
| 5,968,033 A | 10/1999 | Fuller et al. |
| 5,968,034 A | 10/1999 | Fullmer et al. |
| 6,015,404 A | 1/2000 | Altshuler et al. |
| 6,027,495 A | 2/2000 | Miller |
| RE36,634 E | 3/2000 | Ghaffari |
| 6,050,990 A | 4/2000 | Tankovich et al. |
| 6,056,738 A | 5/2000 | Marchitto et al. |
| 6,059,820 A | 5/2000 | Baronov |
| 6,074,382 A | 6/2000 | Asah et al. |
| 6,080,146 A | 6/2000 | Altshuler et al. |
| 6,096,029 A | 8/2000 | O'Donnell, Jr. |
| 6,096,209 A | 8/2000 | O'Brien et al. |
| 6,104,959 A | 8/2000 | Spertell |
| 6,120,497 A | 9/2000 | Anderson et al. |
| 6,149,644 A | 11/2000 | Xie |
| 6,174,325 B1 | 1/2001 | Eckhouse |
| 6,197,020 B1 | 3/2001 | O'Donnell, Jr. |
| 6,235,016 B1 | 5/2001 | Stewart |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,354,370 B1 | 3/2002 | Miller et al. |
| 6,508,813 B1 | 1/2003 | Altshuler |
| 6,517,532 B1 | 2/2003 | Altshuler et al. |

FOREIGN PATENT DOCUMENTS

| | | |
|---|---|---|
| EP | 0 142 671 | 5/1985 |
| EP | 0 565 331 | 10/1993 |
| EP | 0 598 984 A1 | 6/1994 |
| EP | 0 724 894 | 8/1996 |
| EP | 0 726 083 | 8/1996 |
| EP | 0 736 308 | 10/1996 |
| EP | 0 755 698 | 1/1997 |
| EP | 0 763 371 | 3/1997 |
| EP | 0 765 673 | 4/1997 |
| EP | 0 765 674 | 4/1997 |
| EP | 0 783 904 A2 | 7/1997 |
| EP | 1 038 505 A | 9/2000 |
| EP | 1 219 258 A1 | 3/2002 |
| FR | 2 591 902 | 7/1987 |
| GB | 2 044 908 A | 10/1980 |
| GB | 2 123 287 A | 2/1982 |
| GB | 2 360 946 A | 10/2001 |
| RU | 95105406 | 6/1997 |
| RU | 94012665 | 10/1997 |

| | | |
|---|---|---|
| RU | 94040344 | 10/1997 |
| RU | 95102749 | 11/1997 |
| RU | 4954402 | 10/1998 |
| SU | 532304 | 7/1974 |
| SU | 719439 | 8/1975 |
| SU | 741747 | 10/1977 |
| SU | 1257475 A1 | 9/1986 |
| SU | 1326962 A1 | 7/1987 |
| WO | WO86/02783 | 5/1986 |
| WO | WO90/00420 | 1/1990 |
| WO | WO92/16338 | 10/1992 |
| WO | WO92/19165 | 11/1992 |
| WO | WO93/05920 A1 | 4/1993 |
| WO | WO95/15725 A1 | 6/1995 |
| WO | WO95/32441 A1 | 11/1995 |
| WO | WO96/23447 A1 | 8/1996 |
| WO | WO96/25979 A1 | 8/1996 |
| WO | WO97/13458 | 4/1997 |
| WO | WO98/04317 | 2/1998 |
| WO | WO98/24507 | 6/1998 |
| WO | WO98/51235 A1 | 11/1998 |
| WO | WO98/52481 A1 | 11/1998 |
| WO | WO 99/27997 A1 | 6/1999 |
| WO | WO99/29243 A1 | 6/1999 |
| WO | WO99/38569 A3 | 8/1999 |
| WO | WO99/38569 A2 | 8/1999 |
| WO | WO99/46005 A1 | 9/1999 |
| WO | WO 99/49937 A1 | 10/1999 |
| WO | WO00/03257 A1 | 1/2000 |
| WO | WO 00/71045 A1 | 11/2000 |
| WO | WO00/74781 A | 12/2000 |
| WO | WO 00/78242 A1 | 12/2000 |
| WO | WO01/03257 A1 | 1/2001 |
| WO | WO01/34048 | 5/2001 |
| WO | WO 01/54606 A1 | 8/2001 |
| WO | WO 02/53050 A1 | 7/2002 |
| WO | WO 02/094116 A1 | 11/2002 |

OTHER PUBLICATIONS

Amy, Robert L. and Storb, R., "Selective Mitochondrial Damage by a Ruby Laser Microbeam: An Electron Microscopic Study," *Science,* 15:756–758, Nov. 1965.

Anderson, R. Rox, et al., "The Optics of Human Skin," *The Journal of Investigative Dermatology,* vol. 77, No. 1, pp. 13–19, 1981.

Anderson, R. R, and Parrish, J. A., M.D., "Selective Photothermolysis: Precise Microsurgery by Selective Absorption of Pulsed Radiation," *Science,* 220:524–527, 1983.

Belikov, A.V., et al. "Identification of enamel and dentine under tooth laser treatment," *SPIE,* Progress in Biomedical Optics, Europt Series, Proceedings of Medical Applications of Lasers III, vol. 2623, pp. 109–116.

Dover, J. S., et al., "Pigmented Guinea Pig Skin Irradiated with Q–Switched Ruby Laser Pulses," *Arch. Dermatol,* 125:43–49, 1989.

Finkelstein, L. H. and Blatstein, Lee M., "Epilation of Hair–Bearing Urethral Grafts Using the Neodymium: YAG Surgical Laser," *The Journal of Urology,* 146:840–842, 1991.

Goldman, L., "Laser History and Theory," "Laser Instrumentation," and "Summary and Conclusions," Biomedical Aspects of the Laser, New York, Springer–Verlag, 1967, pp iii–11, 220–232.

Goldman, L., "Dermatologic Manifestation of Laser Radiation," *Fed Am Soc Exp Biology,* Suppl. 14:S–92–S–93, 1965.

Goldman, L., "Effects of New Laser Systems on the Skin," *Arch Dermatol,* 108:385–390, 1973.

Goldman, L., "Laser Surgery for Skin Cancer," *NY State J Med,* 77:1897–1900, 1977.

Goldman, L., "Surgery by Laser for Malignant Melanoma," *J. Dermatol. Surg. Oncol.,* 5(2):141–144, 1979.

Goldman, L., "The Skin," *Arch Environ Health,* 18:434–426, 1969.

Goldman, L. and Richfield, D. F., "The Effect of Repeated Exposures to Laser Beams," *Acta Derm.–Veneoral,* 44:264–268, 1964.

Goldman, L. and Rockwell, J., "Laser Action of the Cellular Level," *JAMA,* 198:641–644, 1966.

Goldman, L. and Wilson, R. G., "Treatment of Basal Cell Epithelioma by Laser Radiation," *JAMA,* 189:773–775, 1964.

Goldman, L., et al., "Biomedical Aspects of Lasers," *JAMA,* 188:230–234, 1964.

Goldman, L., et al., "Effect of the Laser Beam on the Skin: Preliminary and Short Report," *The Journal of Investigative Dermatology,* 40:121–122, 1963.

Goldman, L., et al., "Effect of the Laser Beam on the Skin III. Exposure of Cytological Preparations," *The Journal of Investigative Dermatology,* 42:247–251, 1964.

Goldman, L., et al., "Impact of the Laser on Nevi and Melanomas," *Arch Dermatol,* 90:71–75, 1964.

Goldman, L., et al., "Laser Treatment of Tattoos," *JAMA,* 210:163–166, 1967.

Goldman, L., et al., "Long–Term Laser Exposure of a Senile Freckle," *Arch Environ Health,* 22:401–403, 1971.

Goldman, L., et al., "Pathology of the Effect of the Laser Beam on the Skin," *Nature,* 197:912–914, 1963.

Goldman, L., et al., "Preliminary Investigation of fat Embolization from Pulsed Ruby Laser Impacts of Bone," *Nature,* 221:361–363, 1969.

Goldman, L., et al., "Radiation from a Q–Switched Ruby Laser. Effect of Repeated Impacts of Power Output of 10 Megawatts on a Tattoo of Man," *The Journal of Investigative Dermatology,* 44:69–71, 1965.

Goldman, L., et al., "Replica Microscopy and Scanning Electron Microscopy of Lawer Impacts on the Skin," *The Journal of Investigative Dermatology,* 52:18–24, 1969.

Grossman, M. C., et al., "Damage to Hair Follicles by Normal–mode Ruby Laser Pulses," *Journal of the American Academy of Dermatology,* 35(6):889–894, 1996.

Grossman, M. C., et al., "Laser Targeted at Hair Follicles," *Lasers Med Surg.,* Suppl. 7:221, 1995.

Klein, E., et al., "Biological Effects of Laser Radiation I: Threshold Studies and Reversible Depigmentation in Rodent Skin," *Northeast Electronics Research and Engineering Meeting—NEREM Record—1965,* IEEE Catalogue No. F–60, (Nov. 4, 1965) pp. 108–109.

Kuhns, J. G., et al., "Biological Effects of Laser Radiation II: Effects of Laser Irradiation on the Skin," *Northeast Electronics Research and Engineering Meeting—NEREM Record 1965,* IEEE Catalogue No. F–60, (Nov. 4, 1965) pp. 152–153.

Kuhns, James G., et al., "Laser Injury in Skin," *Laboratory Investigation,* vol. 17, No. 1, (Jul., 1967) pp. 1–13.

Manstein, Dieter, et al., "Selective Photothermolysis of Lipid–Rich Tissue," *American Society for Laser Medicine and Surgery Abstracts,* No. 17, American Society for Laser Medicine and Surgery Twenty–First Annual Meeting, Apr. 20–22, 2001, p. 6.

Margolis, R. J., et al., "Visible Action Spectrum for Melanin–Specific Selective Photothermolysis," *Lasers in Surgery and Medicine,* 9:389–397, 1989.

Parrish, J. A., M.D., et al., "Selective Thermal Effects with Pulsed Irradiation from Lasers: From Organ to Organelle," *The Journal of Investigative Dermatology,* 80:75s–80s, 1983.

Polla, L. L., et al., "Melanosomes Are a Primary Target of Q–Switched Ruby Laser Irradiation in Guinea Pig Skin," *The Journal of Investigative Dermatology,* 89:281–286, 1987.

Riggle, Grant C., "Laser Effects on Normal and Tumor Tissue," *Laser Applications in Medicine and Biology,* 1:35–63, 1971.

Shimbashi, T. and Kojima, T., "Ruby Laser Treatment of Pigmented Skin Lesions," *Aesthetic Plastic Surgery,* 19:225–229, 1995.

Stratton, K., et al., "Biological Effects of Laser Radiation II: ESR Studies of Melanin Containing Tissues after Laser Irradiation," *Northeast Electronics Research and Engineering Meeting—NEREM Record—1965,* IEEE Catalogue No. F–60, (Nov. 4, 1965) pp. 150–151.

Taylor, C. R., et al., "Treatment of Tattoos by Q–Switched Ruby Laser," *Arch Dermatol,* 126:893–899, 1990.

Tuchin, Valery V., "Laser Light Scattering in Biomedical Diagnostics and Therapy," reprinted from *Journal of Laser Applications,* vol. 5(2,3), pp. 43–60 (Fall 1993) Laser Institute of America, Toledo, Ohio.

Watanabe, S., et al., "Comparative Studies of Femtosecond to Microsecond Laser Pulses on Selective Pigmented Cell Injury in Skin," *Photochemistry and Photobiology,* 53:757–762, 1991.

Watanabe, S., et al., "The Effect of Pulse Duration on Selective Pigmented Cell Injury by Dye Lasers," *The Journal of Investigative Dermatology,* 88:523, 1987.

Welch, A. J., et al., "Evaluation of Cooling Techniques for the Protection of the Epidermis during ND–YAG Laser Irradiation of the Skin," *Neodymium–YAG Laser in Medicine and Surgery.* New York, Elsevier, 1983, pp 196–204.

Yules, R. B., et al., "The Effect of Q–Switched Ruby Laser Radiation on Dermal Tattoo Pigment in Man," *Arch Surg.* 95:179–180, 1967.

Zeitler, E. and Wolbarsht, M. L., "Laser Characteristics that Might be Useful in Biology," *Laser Applications in Medicine and Biology,* 1:1–16, 1971.

Abstracts Nos. 17–19, Lasers in Surgery and Medicine, ASLMS, Supplement 13, 2001.

Abstracts Nos. 219–223, ASLMS.

Abstracts, various.

LIGHT ENERGY DELIVERY HEAD

PRIOR APPLICATIONS

This application is a continuation of application Ser. No. 09/473,910, filed Dec. 28, 1999, now U.S. Pat. No. 6,517,532 which claims priority from provisional specification No. 60/115,447, filed Jan. 8, 1999; from provisional specification No. 60/164,492, filed Nov. 9, 1999; and which is also a continuation-in-part of application Ser. No. 09/078,055 now U.S. Pat. No. 6,273,884, filed May 13, 1998, which application claims priority from provisional specification Nos. 60/046,542, filed May 15, 1997 and 60/077,726, filed Mar. 12, 1998. The contents of all of these prior application specifications are incorporated herein by reference.

FIELD OF THE INVENTION

This invention relates to light energy delivery heads, and more particularly to a laser diode head or other light energy delivery head for delivering light energy to a selected depth in a medium, particularly a scattering medium, which head provides improved heat management for both the laser diodes (or other light energy emitter) and the medium and/or which more efficiently utilizes light energy from the laser/emitter.

BACKGROUND OF THE INVENTION

Light energy emitters, including lasers, and in particular semiconductor diode lasers, flash lamps, halogen and other filament lamps, etc., are finding increasing application in medical, industrial, research, governmental and other applications. For many of these applications, the light energy is to be delivered at a selected depth in a light scattering medium. Because of the scattering, only a fraction of the light energy delivered to the surface of the medium reaches the target area, with much of the remaining energy being refracted out of the medium and dissipated in the surrounding atmosphere. For a highly scattering medium such as skin, as much as 50–80 percent of the incident energy may be lost due to this back scattering effect, requiring more powerful light energy emitters/lasers or a larger number of emitters/diodes lasers (where diode lasers are used), or requiring that light energy be delivered over a much smaller area, in order to achieve a desired fluence at a target. Utilizing a head with a more powerful emitter/laser or utilizing a larger number of and/or more powerful emitters/diode lasers makes the head larger and more expensive and increases the heat management problems resulting from use of the head. Concentrating the beam to achieve higher fluence with smaller spot size or aperture adversely affects the depth in the medium which can be reached by the light energy and can significantly increase the time required to perform a given procedure.

U.S. Pat. No. 5,824,023, to Rox Anderson, teaches one way of dealing with the reflection problem with certain laser or other light energy emitting devices. However, the technique of this patent also results in small spot sizes and is not readily adaptable for use in certain applications, such as in laser diode heads. An improved technique is therefore required to permit optimum utilization of the light energy from light energy emitting devices in general, and from laser diodes or laser diode bars of a laser diode head in particular, by recycling or reusing light scattered from the surface of the irradiated medium and directing it back toward a desired target area in the medium.

A related problem involves heat management when using a laser diode head, or other head containing light energy emitters, and in particular the ability to utilize a common cooling element to cool both the laser diodes/light energy emitters and the surface of the medium being irradiated. Surface cooling can be required in various applications, particularly medical applications, since laser energy being delivered at a depth in the medium, for example a patient's skin, must pass through the surface of the medium, for example the epidermis of a patient's skin, in order to reach the target area. Heating of the medium surface can cause damage at the surface if suitable cooling is not provided. Prior art systems have either not provided cooling for the medium surface or have required separate cooling elements for the diodes and the medium.

SUMMARY OF THE INVENTION

In accordance with the above, this invention provides, in a first aspect, a head for applying light energy to a selected depth in a scattering medium having an outer layer in physical and thermal contact with the head. The head includes a thermally conductive block or mount having an energy emitting surface; at least one laser diode or other energy emitting element mounted in the block adjacent the energy emitting surface, each of the elements being in thermal contact with the mount and being oriented to direct light energy through the energy emitting surface. A thin, transparent, thermally conductive layer is provided over the light emitting surface and in thermal contact therewith, the layer being in contact with the outer layer of the medium when the head is applying light energy thereto. Finally, a cooling mechanism is provided for the mount, permitting the mount to sink heat from both the elements and the outer layer of the medium. For some embodiments, the thermally conductive layer is a coating formed on the light emitting surface of the mount.

For preferred embodiments, the head also includes a reflecting layer formed on the thermally conductive layer, which reflecting layer has an opening formed therein under each element through which light energy may be applied to the medium. The reflecting layer is preferably between the thermally conductive layer and the energy emitting surface of the mount/block, and preferably has an area larger than the area of the block. In particular, the area of the reflecting layer could be at least substantially as large as the aperture of reflection for scattered light energy from the medium. In order to achieve a desired amplification coefficient (f) as a result of retroreflection from the reflecting layer, the aperture through which light energy is applied to the medium should have a minimum $$D_{min} = \frac{d}{\sqrt{\frac{f \cdot R \cdot r}{f-1} - 1}}$$

dimension where d is a back-scatter aperture increment for a given wavelength and medium, R is the reflection coefficient of the medium and r is the reflection coefficient of the reflecting layer.

The block for the laser diode head may assume a variety of forms. In particular, for some embodiments of the invention, the block has a depression formed therein, with the energy emitting surface being the surface of the depression, and with each of the elements for some embodiments being mounted to emit light energy substantially perpendicular to the depression surface at the point thereon where the element is mounted. The medium is forced into the depression and into contact with the surface thereof. The forcing of medium into the depression may be accomplished by merely pressing the head against a soft deformable medium, such as some areas of a person's skin, or suction, for example a vacuum line, may be provided to draw the skin or other medium into the depression. The depression may have a variety of shapes, including being substantially semi-cylindrical or substantially rectangular. Where the head is being utilized for hair removal on for example a person, the depression may be of a size sufficient to permit a single hair follicle to enter the depression in the plane of the rectangular depression.

The reflecting layer may also be formed and utilized for heads which use the cooled block to cool the diodes or other light energy emitters only and not to cool the surface of the medium, for example in applications where a thicker transparent layer is employed or for heads using light energy emitting elements other than laser diode bars, for example filament lamps or light pipes fed by a suitable light emitting component. For such heads, the reflecting layer would still have areas of the type indicated above and would preferably have an emitting aperture with a minimum dimension $D_{min}$ determined as indicated above. For these embodiments, the transparent layer could be a waveguide of selected shape, which shape could be a truncated shape which, depending on desired aperture size, would have either its larger end or shorter end adjacent the block. Selected sides or walls of the waveguide may have an angle dependent reflecting layer to attenuate sharply angled light energy entering the waveguide.

In still another aspect of the invention, the head may include at least one energy emitting element mounted to apply light energy to the medium through an aperture, which aperture has a minimum dimension $D_{min}$ defined as indicated above, and a reflecting layer mounted to retroreflect light energy back-scattered from the medium. The aperture may be circular, with D being a diameter of the aperture, or substantially rectangular, with D as the length of a short side of the aperture.

The foregoing and other objects, features and advantages of the invention will be apparent from the following more specific description of preferred embodiments of the invention as illustrated in the accompanying drawings.

IN THE DRAWINGS

DETAILED DESCRIPTION

Figure 1:
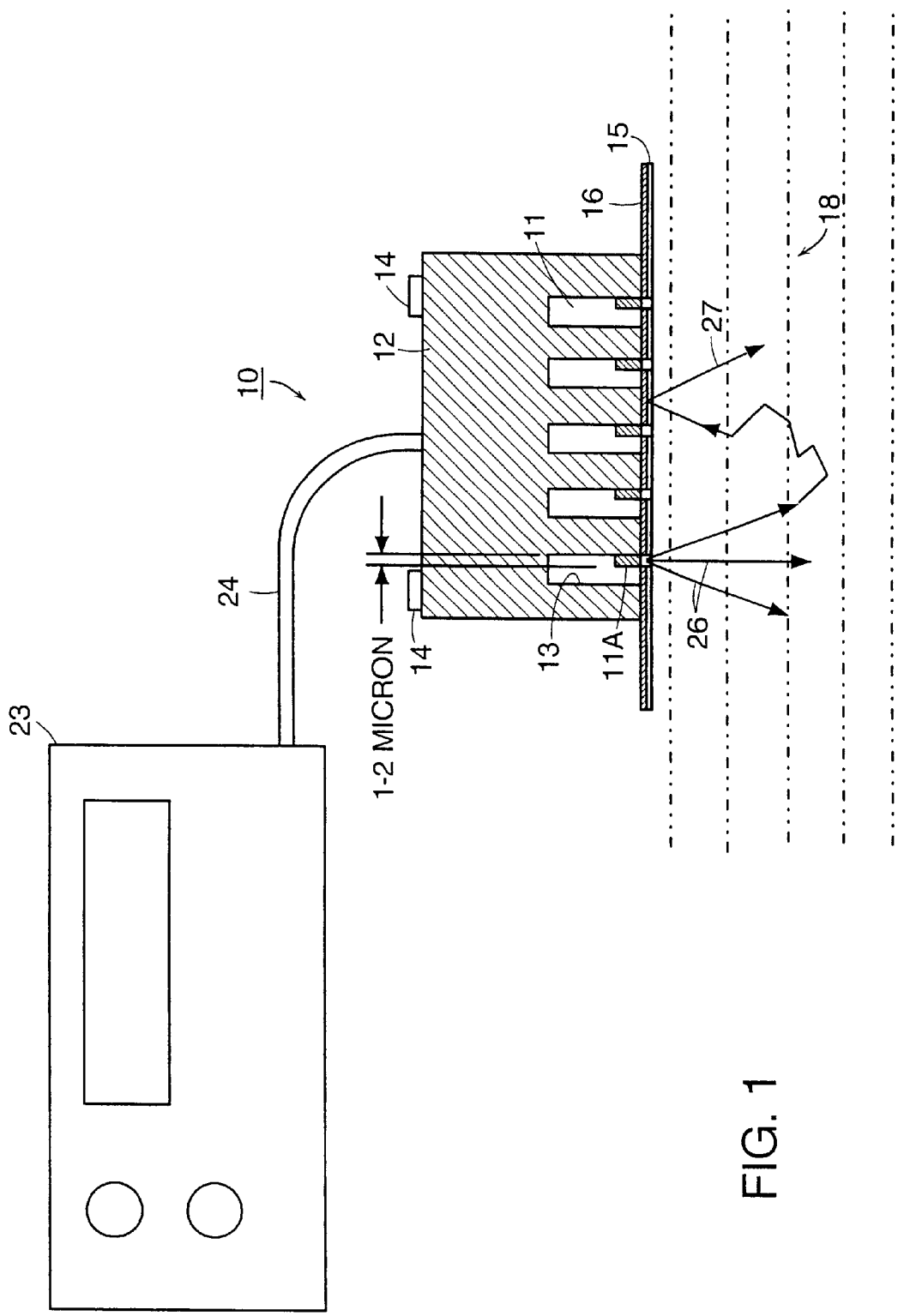
FIG. 1 is partially cutaway, side elevation, semi-schematic representation of a head in accordance with a first embodiment of the invention.

Referring first to FIG. 1, a laser head 10 is shown which contains a plurality of laser diode bars 11, each of which includes a plurality of emitters 11A and is mounted in a groove 13 formed in a block 12. Block 12 may be formed of one or more materials having good thermal conduction properties, and may be fabricated in a number of ways, all of which are within the contemplation of this invention. In particular, block 12 may be formed of a single material which, in addition to having good thermal conduction properties, is also an electrical insulator, with the side walls of grooves 13 being coated or plated with an electrically conducting material and the diode bars soldered in the grooves, an electrical circuit being formed between adjacent grooves so that current may flow through the diodes without being shorted through block 12. Alternatively, the portion of block 12 between grooves 13 may be fabricated of electrically conductive mounts which are secured in a suitable way to a thermally conducting and electrically insulating substrate, the conducting mounts providing an electrical path through the diodes and the insulating substrate preventing shorts. Other techniques for providing an electrical path through the diodes to permit selective energization thereof, while not provided a short circuit path through block 12 may also be employed.

Block 12 serves as a heat sink for diode bars 11 and a variety of techniques may be utilized to remove heat from block 12. These include providing one or more channels through block 12 and flowing a fluid, which is generally water but may be some other liquid or gas, through the channel to remove heat from block 12. Alternatively, one or more thermoelectric components 14, for example Peltier elements, may be attached to block 12 and utilized to remove heat therefrom.

A transparent element 15 having a high reflectivity mask 16 attached thereto is mounted to the bottom of block 12, with mask 16 preferably being between block 12 and element 15. For a preferred embodiment where head 10 is being used for dermatological treatment, the scattering media 18 being the skin of a patient, the transparent element is preferably formed of sapphire or some other material having a good index match with skin, and is preferably either a sapphire coating which is for example 1 to 2 microns thick, or a sapphire plate or wafer which is for example 1 to 2 mm thick. If component 15 is a plate or wafer, then mask 16 may be a coating of a highly reflective material such as Ag, Cu, Au or a multilayer dielectric coating which is formed using an appropriate coating technology known in the art, such as lithography, on the plate/wafer 15. Openings 20 (FIG. 2A) are formed in the coating 16 under each of the diode bar emitter 11A, the openings 20 being only large enough to permit light from the diode bars to pass unobstructed therethrough. Keeping slits or openings 20 in reflective layer or mask 16 as small as possible is desirable in that it maximizes the reflectivity of the mask and thus, as will be discussed later, optimizes retroreflection of scattered energy from skin or other media 18. For reasons which will be discussed in greater detail later, reflective layer 16 should have a larger footprint than block 12 to further enhance the reflection back into the media 18 of scattered light or energy emitted therefrom. Since for the illustrative embodiment, mask 16 is supported on transparent plate or wafer 15, this component also has a larger profile. Alternatively, mask 16 may be a thin plate or wafer having slits 20 formed therein, and transparent component 15 may be a layer of for example sapphire having a thickness in the 1 to 2 micron range which is coated thereon. In this case, the coating need not extend beyond the dimensions of block 12; however, it is preferable that this coating extend for the full dimensions of mask 16 to provide a good optical index match for retroreflected light.

Finally, the apparatus of FIG. 1 includes a box 23 connected to head 10 by suitable electrical lines and, where appropriate, plumbing lines (for cooling water) 24. Box 23 may contain appropriate power supplies for diodes bars 11, control circuitry, fluid pumps where fluid cooling is utilized and other appropriate components. The specific components contained in box 23 do not form part of the present invention.

The apparatus of FIG. 1 has several advantageous features over the prior art. First, where the medium 18 is the skin of a patient undergoing a dermatological procedure, such as for example the removal of a tattoo, a port wine stain, blood vessel, or other vascular lesion, or hair removal, it is desirable to cool the epidermis, the surface layer of the skin, to prevent thermal damage thereto during the procedure. In the prior art, a cooling mechanism has been provided for the epidermis in particular, and for the surface area of a patient's skin in general, which cooling mechanism is separate and independent from the cooling mechanism utilized to sink heat from diode bars 11. These separate cooling mechanisms add to the size, weight, complexity and cost of the system in general, and of the delivery head 10 in particular. The embodiment of FIG. 1 overcomes these problems by having at most a few millimeters of material between the block 12, which is cooled by thermoelectric components 14, by a flowing fluid, and/or by other suitable means, and the patient's skin. Further, the sapphire typically used for transparent component 15 has good thermal transfer properties so that heat from the patient's skin may easily flow to cooled block 12, and this block may serve as a heat sink for both diode bars 11 and the epidermis of a patient's skin or other surface area of a media 18 to which light energy is being applied. This arrangement is more compact, simpler and less expensive than prior art heads performing the same function.

Further, as illustrated in the Figure, light energy emitted from a diode bar 11 in the form of rays 26 is scattered in media 18, for example in a patient's skin, and at least some of this energy, perhaps 70 percent, depending on the pigmentation of the patient's skin, is reflected back and exits the patient's skin at some angle. Substantially all of this light impinges on reflecting surface or mask 16, and, since this mask has a reflectivity approaching 100 percent, substantially all of this light energy is retroreflected back into the skin. This retroreflection results in a roughly 300 percent increase in the light energy or fluence reaching a target at a selected depth in the patient's skin for a given fluence emitted from diode bars 11. This means that either the same therapeutic results can be achieved using less diode bars 11 or lower energy diode bars 11 or that higher energy, and therefore more effective treatment, can be achieved using the same number and power of diode bars. More effective results can thus be achieved for a given size, cost and complexity of the diode laser head.

Figure 10B:
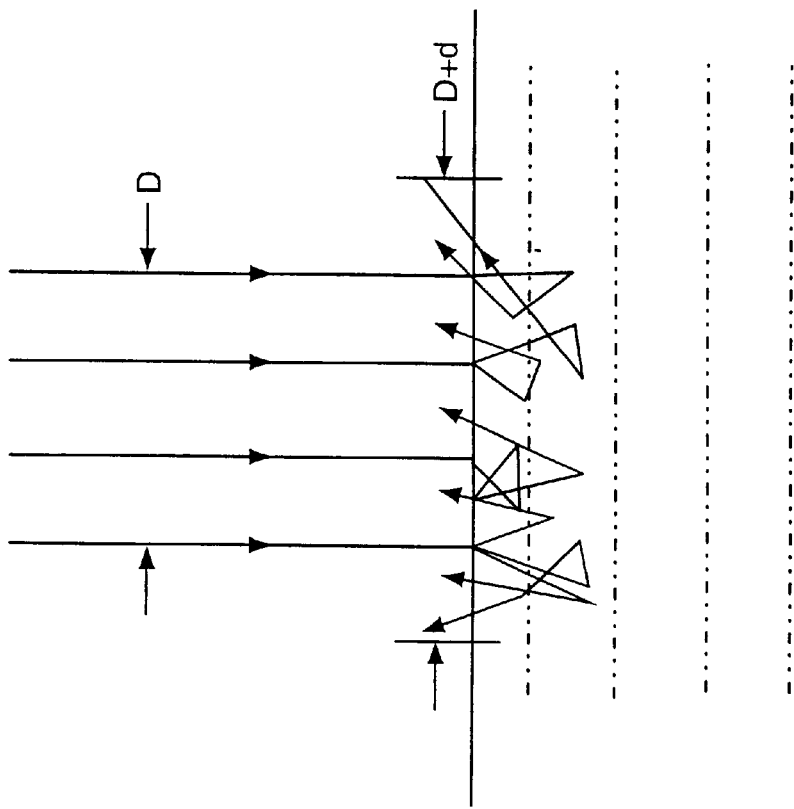
FIGS. 10A and 10B are graphic representations illustrating the back scattering effect for a narrow and a wide beam respectively.
Figure 10A:
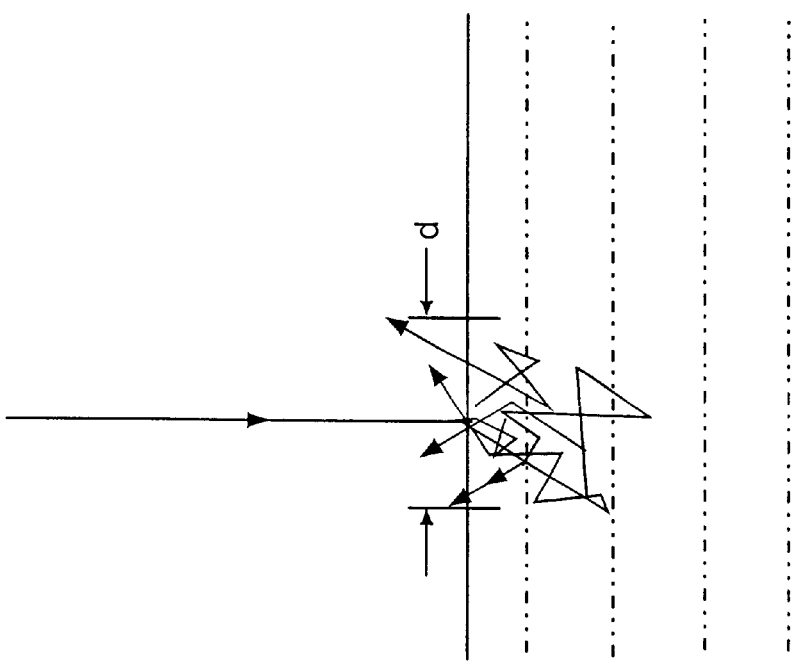
Figure 11:
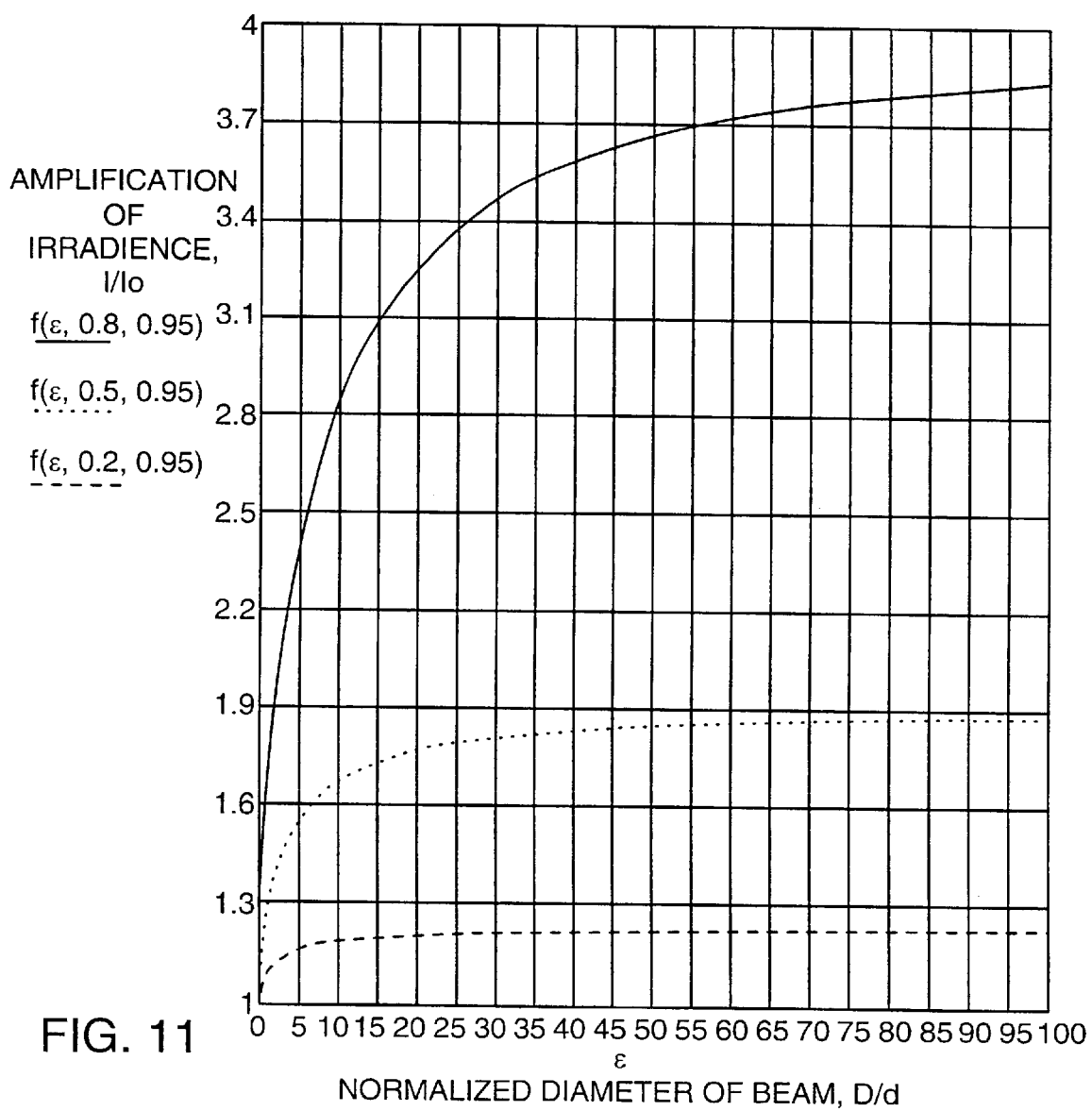
FIG. 11 is a graphic representation of the relationship between a coefficient for amplification of irradiance in a scattering medium and beam diameter for three mediums having different diffuse reflecting characteristics.

Further, as illustrated in FIG. 10B, light energy entering scattering medium 18 over an aperture of size D will, because of beam divergence and scattering, exit the medium over an aperture D+d, where d is a back-scatter aperture increment and is substantially constant for a given beam wavelength and medium, regardless of the input aperture D. This is illustrated by FIGS. 10A and 10B, where d is substantially the same for a thin beam which substantially enters the medium 18 at a single point and for a wide beam having an aperture D. Thus, as the aperture size D increases, d becomes a smaller percentage of the reflection aperture D+d. For a generally circular aperture, D and D+d are diameters, while for a generally rectangular aperture, these values may be considered to be the length of the smaller side of the rectangle.

The reflection by reflective mask 16 can increase the amount of energy reaching a desired target area by several times. This increase in effective usage of light energy can be quantitatively described by the increase in illumination inside scattering medium 18, this increase being the ratio (f) between the illumination at an arbitrary target point inside the scattering medium when the reflected light is returned back to the medium ($I_R$) and when it is not ($I_O$) (i.e., $f=I_R/I_O$). The value of f depends on the reflectance coefficient R of the scattering medium 18 and the coefficient of reflection of the reflecting mask 16 (r) which returns the scattered light back into the medium (i.e., f=1/1−Rr). However, this known dependence does not take into account the influence of beam aperture D; since the beam aperture increases by d as a result of scattering, amplification coefficient f has a strong dependence on the aperture D of the incident beam. In particular, in accordance with the teachings of this invention, it has been determined that when beam aperture is taken into account, the amplification coefficient f can be approximated by the following equation:

$$f = \frac{1}{1 - Rr\left(\frac{D/d}{1+D/d}\right)^2} \quad (1)$$

Using equation 1 for a given medium, a given reflector, and a desired illumination amplification, a minimum beam aperture ($D_{min}$) can be determined. $D_{min}$ is generally given by:

$$D_{min} = d \cdot \frac{1}{\sqrt{\frac{f \cdot R \cdot r}{f-1} - 1}} \quad (2)$$

For f=2, this minimum reduces to $$D_{min} = d \cdot \frac{1}{\sqrt{2 \cdot R \cdot r} - 1} \quad (3)$$

With light skin as a reflecting medium, and an incident beam in the red region of the spectrum, the values in the above equation would be R≈0.7 and d≈3 mm. Assuming a reflector with r≈0.95 would then result in a $D_{min}$=19.5 mm. This suggests that for most applications in laser dermatology, the beam diameter or other appropriate dimension (D) should be greater than 20 mm in order for retroreflection to provide desired illumination amplification. This is illustrated in FIG.

11 where (f) is shown as a function of the ratio D/d for three reflection environments, with r being 0.95 in each instance, and with R equaling 0.2, 0.5 and 0.8, respectively. It is seen that, particularly for the highly scattering medium having R=0.8, f continues to increase with increasing input aperture size and may, with retroreflection, provide up to 3.8 times the intensity achieved without retroreflection. Assuming d is equal to 3 mm, an input aperture of 20 mm would result in well over two times the illumination at the target than if retroreflection were not utilized, and a smaller aperture, for example D=15 mm, would still provide significant amplification. Thus, while each individual diode bar 11 produces a beam having a dimension in the micron range, head 10 can be designed to provide a beam having a dimension D which is sufficient to provide a desired illumination amplification. The reflecting surface 16 is preferably made large enough so as to fully cover the reflection aperture which consists of D+d, but may require little or no extension beyond the end of block 12 where D is large relative to d.

The embodiment shown in FIG. 1 thus provides at least three significant advantages over prior art laser diode heads. First, it provides a very efficient mechanism for cooling both the laser diodes and the surface of medium 18 by use of the same cooling mechanism. Second, it provides a simple and effective mechanism for retroreflecting light scattered from medium 18 over the entire scattering aperture from such medium; and third it provides a beam aperture which is large enough for efficient illumination amplification as a result of retroreflection while using radiation sources, for example laser diode bars, which individually provide small beam apertures in the micron range.

Figure 2B:
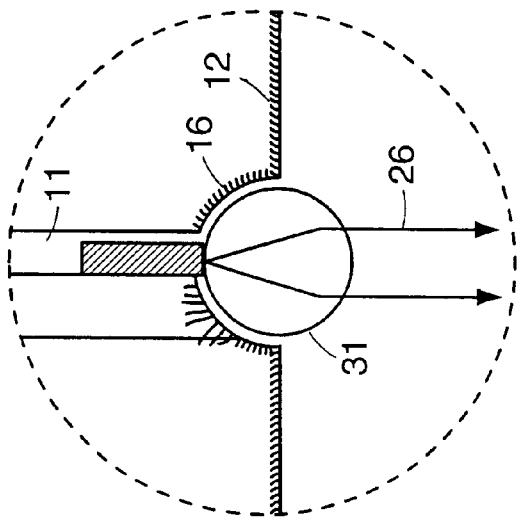
FIGS. 2A and 2B are enlarged side elevation views of a portion of the head shown in FIG. 1 for two different species thereof.
Figure 2A:
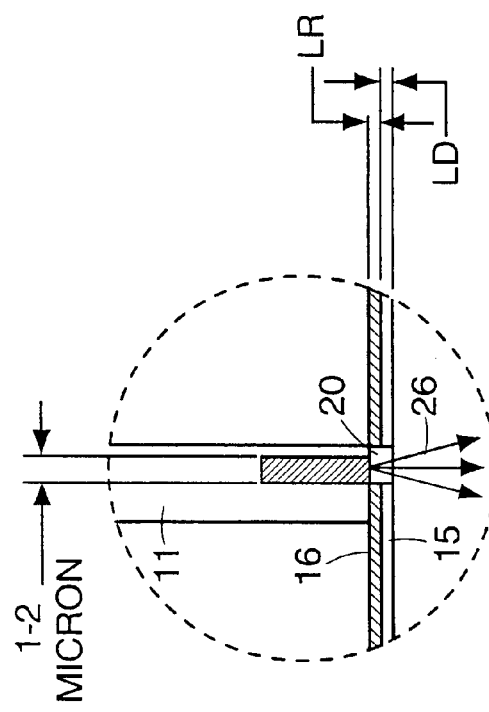

FIG. 2B illustrates an alternative embodiment of the invention which may be useful in some applications. The embodiment of FIG. 2B differs from that of FIG. 2A in that transparent layer 15 has been replaced by a cylindrical lens 31 mounted under each of the laser diode bars 11. Cylindrical lenses 31 can be supported to the array in ways known in the art including a support bracket or other support structure, either mounted to or forming part of block 12 at opposite ends of each cylindrical lens 31. Block 12 also extends somewhat below the bottom of diode bars 11 so as to supply structural support for lenses 31 and to permit block 12 to contact the upper surface of medium 18 when slight pressure is applied to block 12 so that the block may still function to cool the surface of the medium. A reflective coating 16 is formed on the bottom wall of block 12 in all areas thereof except the areas directly under diode bar emitters 11A, the reflective coating otherwise extending substantially around the entire wall of the recess in which lens 31 is positioned. Depending on its diameter, a lens 31 may function to collimate beam 26 emanating from the corresponding diode bar 11 into parallel rays, as opposed to diverging rays as shown in FIG. 2A, or to converge such beams toward a focal point which is preferably at the target depth. Such a collimating or converging of beam 26 reduces the ill effects of scattering on the beam, but does not eliminate such scattering or significantly reduce the need for reflective surface 16.

Figure 3B:
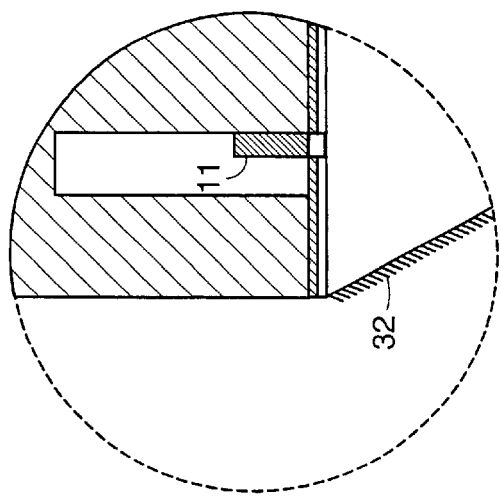
FIG. 3A is a cutaway, side elevation, semi-schematic representation of a head for a first species of a second embodiment, FIG. 3B being an enlarged side elevation view of a portion of the head shown in FIG. 3A.
Figure 3A:
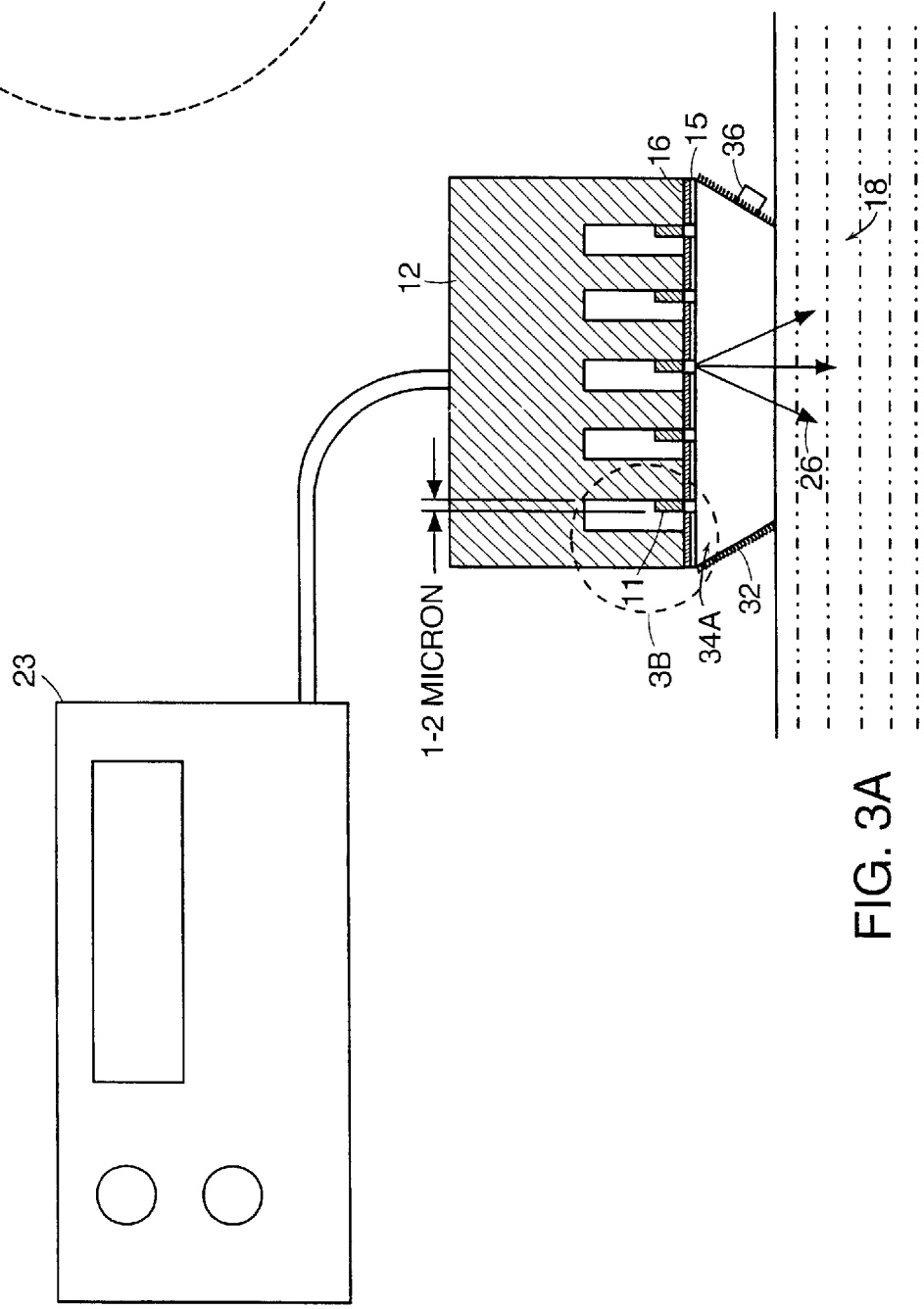

FIG. 3 shows an embodiment which differs from that of FIG. 1 in that higher fluence is required than is provided by the diode bars alone, even with retroreflection. Therefore, energy emitted from transparent layer 15 is applied to a standard concentrator 34A, which may be a hollow truncated cone or prism, but is preferably a block or slab of material having a good index match and good heat transfer properties to the medium 18, for example sapphire when the medium is human skin. Concentrator 34A sacrifices aperture size in order to achieve higher fluence in a manner known in the art. However, the aperture size is maintained sufficient to conform to the requirements specified in equation (2) above in order to maintain the energy amplification effects of retroreflection.

The embodiment of FIG. 3 also deals with a second problem in that scattered light is emitted from the skin at a variety of angles and is returned to the skin generally at the same angle received. This results in a higher concentration of optical energy at the surface of the skin where all beams are received and lower energy at depth, where the desired target is generally located, sharply angled beams only appearing at the surface. Since energy concentrated at the skin surface serves no useful therapeutic purpose and can cause thermal damage or discomfort if not adequately cooled, it is desirable to reduce or eliminate such sharply angled reflected beams, while not interfering with beams reflected at angles substantially perpendicular to the medium surface and returned to the skin at these angles. This objective is accomplished for the embodiment of FIG. 3 by providing a coating 32 on the side walls of concentrator 34A, which coating has angle-dependent reflection characteristics and may have significantly lower reflectivity than reflective surface 16. This means that the sharply angled beams impinging on surface 32 are attenuated or eliminated, thereby reducing the beams entering medium 18 at a sharp angle, these beams being only harmful and producing no useful therapeutic effect.

While the embodiment of FIG. 3 has the advantages discussed above, it also has two potential disadvantages. First, the aperture for receiving reflected radiation is smaller than the aperture (i.e., D+d) of reflected radiation, so that this embodiment does not collect all reflected radiation and retroreflect it to medium 18. This results in a slight decrease in the intensity amplification ratio (f) for this embodiment; however, this disadvantage is mitigated by the fact that much of the energy lost for this embodiment is energy at angles which, even if retroreflected, only contribute to heating the surface of medium 18 and do not to have a therapeutic effect or do other useful work at a target area located at a selected depth in the medium. D being larger than (d) also minimizes this loss. If desired, reflective extensions could also be provided for this embodiment to retroreflect all reflected energy.

The second disadvantage is that, depending on the thickness of concentrator 34A, cooled block 12 may not be effective for cooling the surface of medium 18. In particular, the time (t) it takes to remove heat from a slab of material having one side in good thermal contact with the surface to be cooled, an opposite side in good thermal contact with the cooling medium, in this case the block 12, and a distance or thickness (l) therebetween is $$t\_l^2/\alpha \quad (4)$$

given by:
where $\alpha$ is the dielectric slab temperature conductivity coefficient. Where energy is being applied to the slab as successive laser pulses spaced by a time $t_p$, the slab thickness l for $$l < \sqrt{\alpha \cdot t_p} \quad (5)$$

cooling to be affected is generally given by:
Where the dielectric layer through which optical energy is transmitted and through which it is desired to perform cooling is formed of sapphire having a maximum $\alpha = 15 \cdot 10^{-6}$ m$^2$/s, and for a typical interval between pulses of 0.25 s, this would result in the combined thickness for transparent layer 15 and concentrator 34A of less than 1.9 mm. Therefore, block 12 being utilized to cool both diode bars 11 and the surface of medium 18 would normally not be feasible when a concentrator 34A is utilized and, if cooling is required, it would normally be achieved by providing a separate cooling mechanism, for example one or more thermoelectric cooling elements 36, in contact with concentrator 34A, and preferably near the lower surface thereof. While only a single such cooling element is shown in FIG. 3, typically four or more such elements would be provided, spaced substantially evenly around the periphery of concentrator 34A, to provide uniform cooling thereof.

Figure 4:
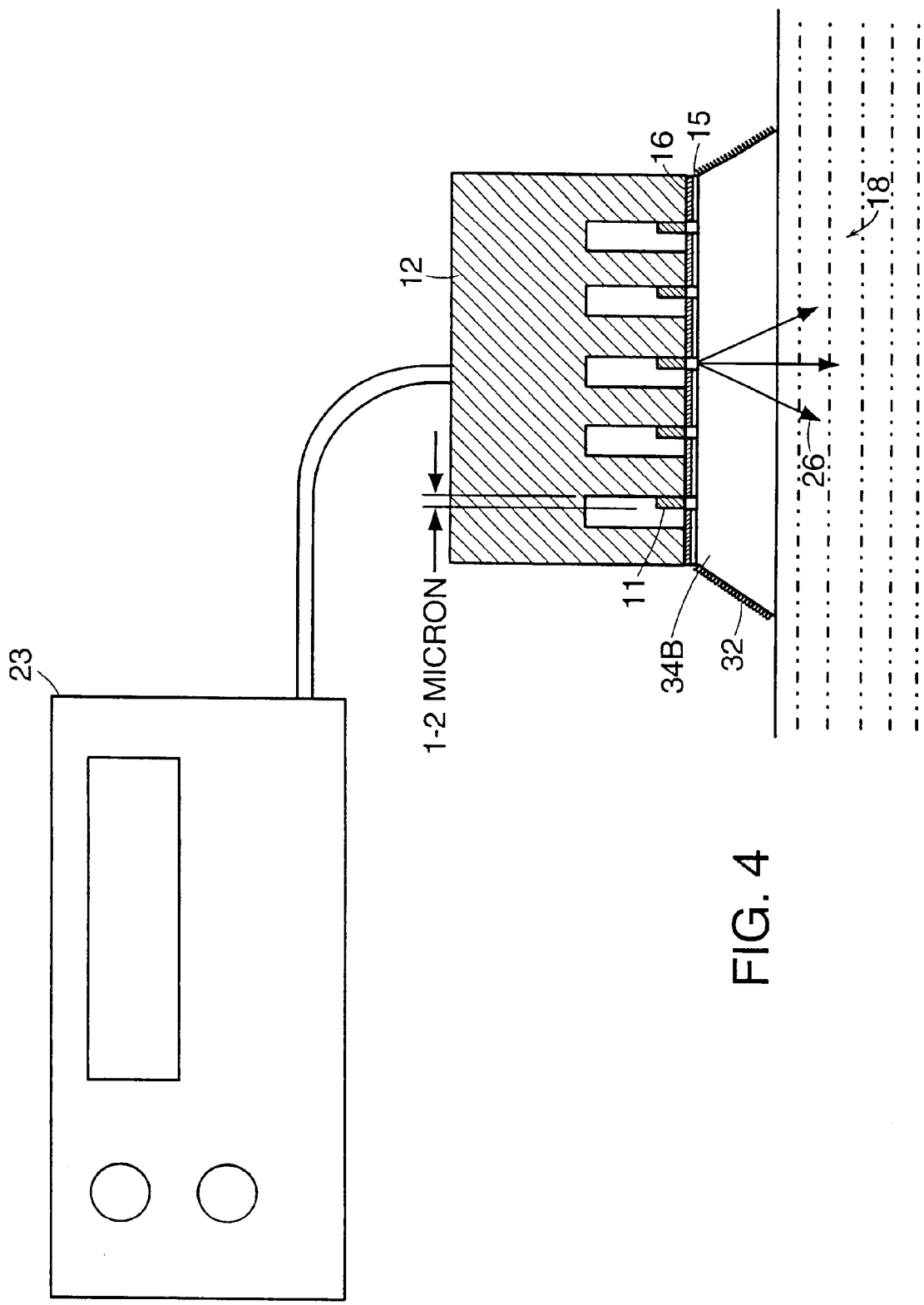
FIG. 4 is a cutaway, side elevation, semi-schematic representation of a second species of the second embodiment of the invention.
Figure 5B:
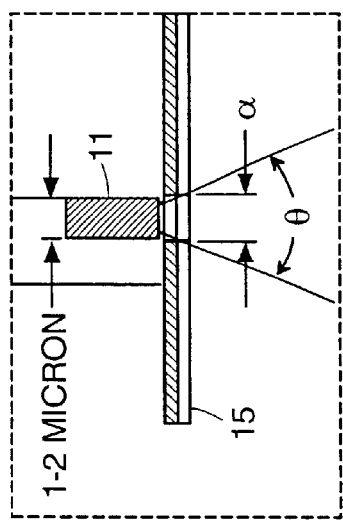
FIG. 5A is a cutaway, side elevation, semi-schematic representation of a third species of the second embodiment of the invention, FIG. 5B being an enlarged, side elevation view of a portion of the species shown in FIG. 5A.
Figure 5A:
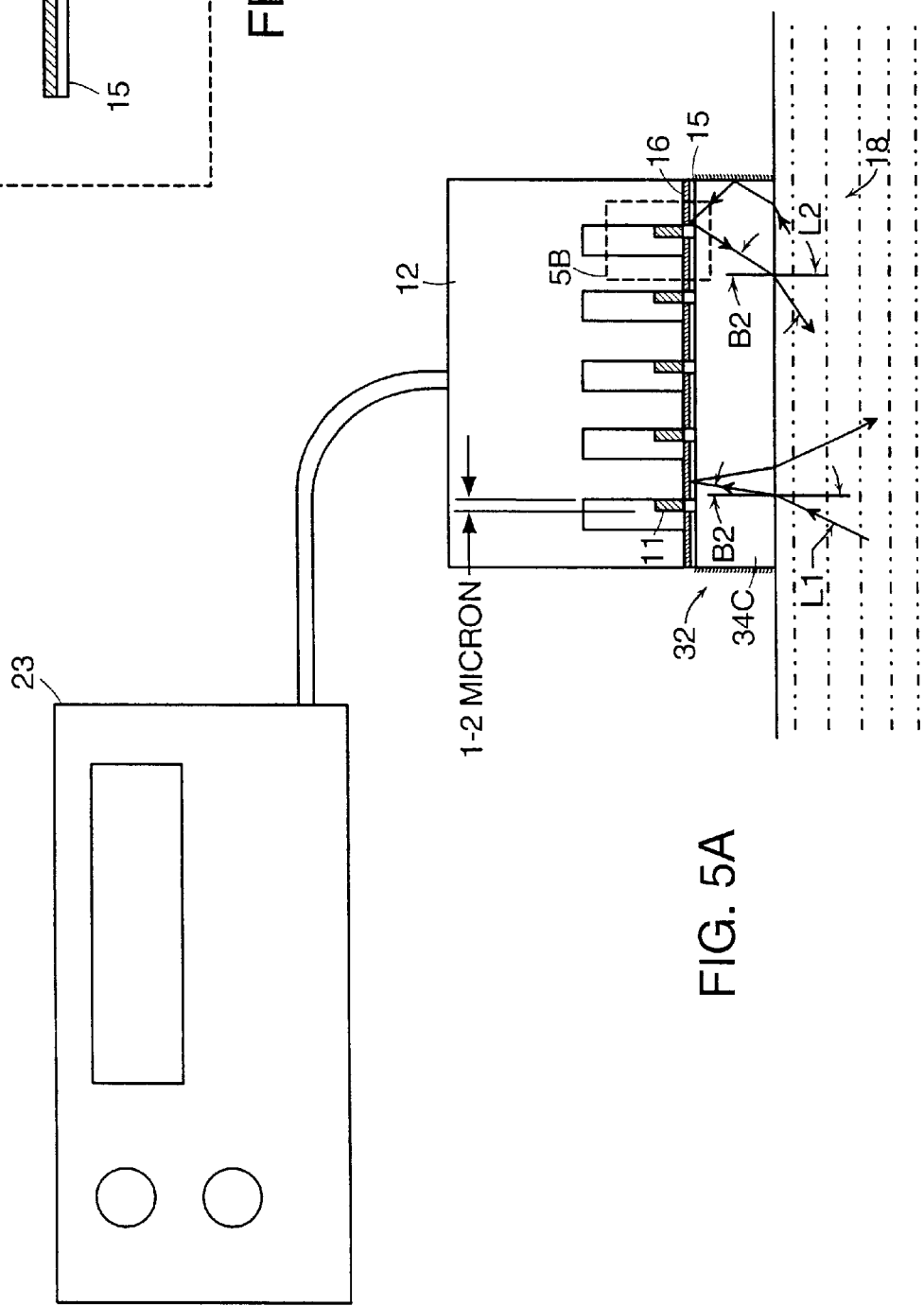

FIGS. 4 and 5 illustrate two additional embodiments of the invention which differ from that shown in FIG. 3 only in that, in FIG. 4, slab 34B is an expander rather than a concentrator, while in FIG. 5, slab 34C has parallel walls so as to not function either as a concentrator or an expander. Slabs 34A, 34B and 34C therefore permit a single block 12 with diode bars 11, transparent layer 15 and reflective layer 16 to be used to achieve a variety of programmable fluence levels. The embodiment of FIG. 4 is advantageous in that it permits more of the scattered light emitted from the surface of medium 18 to be collected and recycled than the other embodiments, with the embodiment of FIG. 5 having intermediate scattered light collecting capabilities. All three embodiments can have angle-dependent reflecting side walls 32 so as to reduce or substantially eliminate light being emitted at sharp angles. While the reduced reflection of surfaces 32 may be uniform, it is preferable that the reflectance from these surfaces be angle-dependent so that light impinging on these surfaces at sharper angles are more heavily attenuated, while light impinging on these surfaces at lesser angles, and therefore light which is more nearly emitted from the surface in a perpendicular direction, are attenuated much less, or in other words are more fully reflected. Further, reflecting surface 16 for all embodiments can also be angle-dependent, reflecting more strongly for light coming in at substantially perpendicular angles than for light coming in at sharper angles. While this may be achieved with a single layer coating, it is preferably achieved with a multilayer coating.

Figure 6:
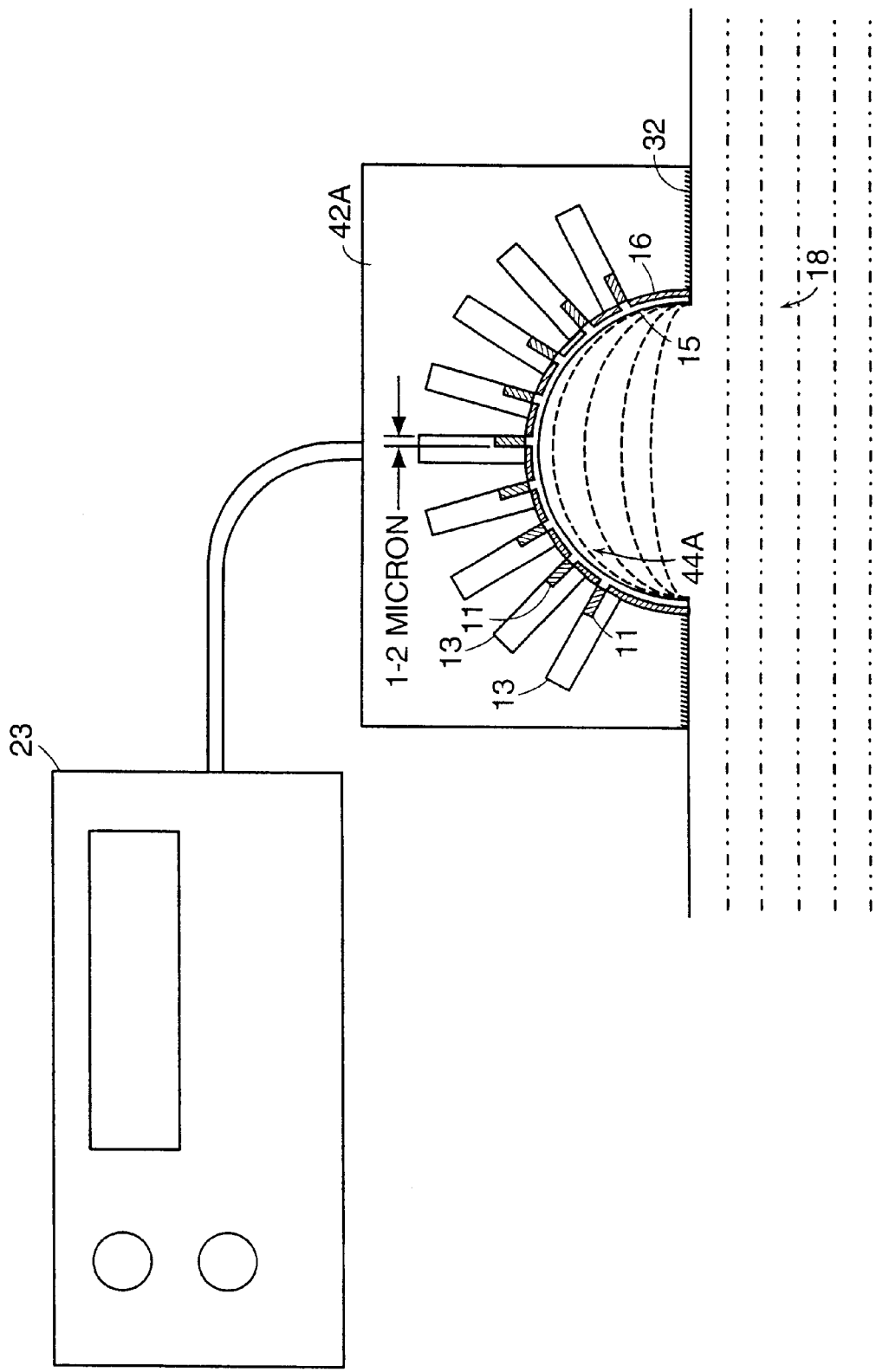
FIG. 6 is a cutaway, side elevation, semi-schematic representation of a first species for a third embodiment of the invention.
Figure 7:
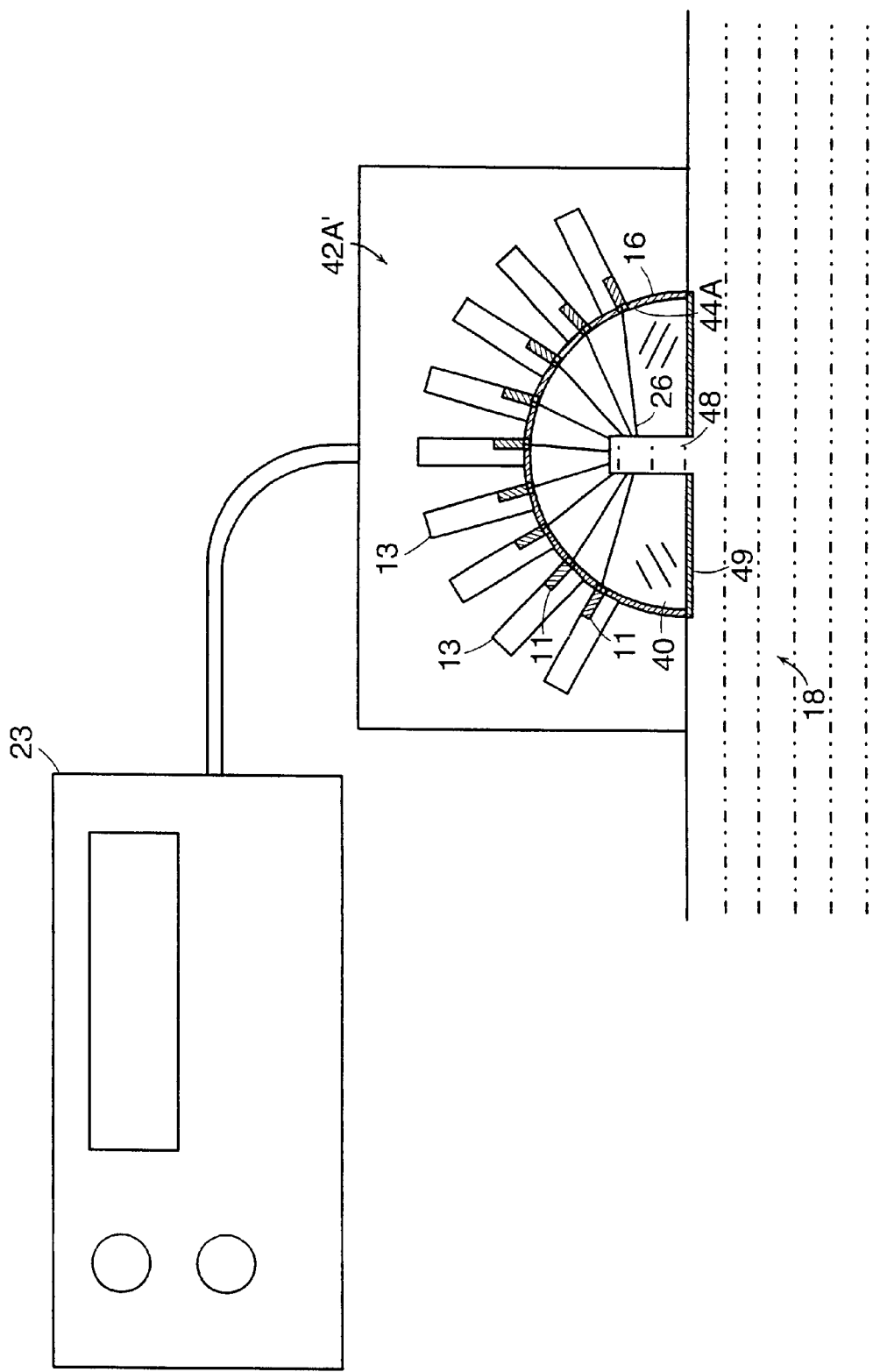
FIG. 7 is a cutaway, side elevation, semi-schematic representation of a second species for the third embodiment of the invention.
Figure 8:
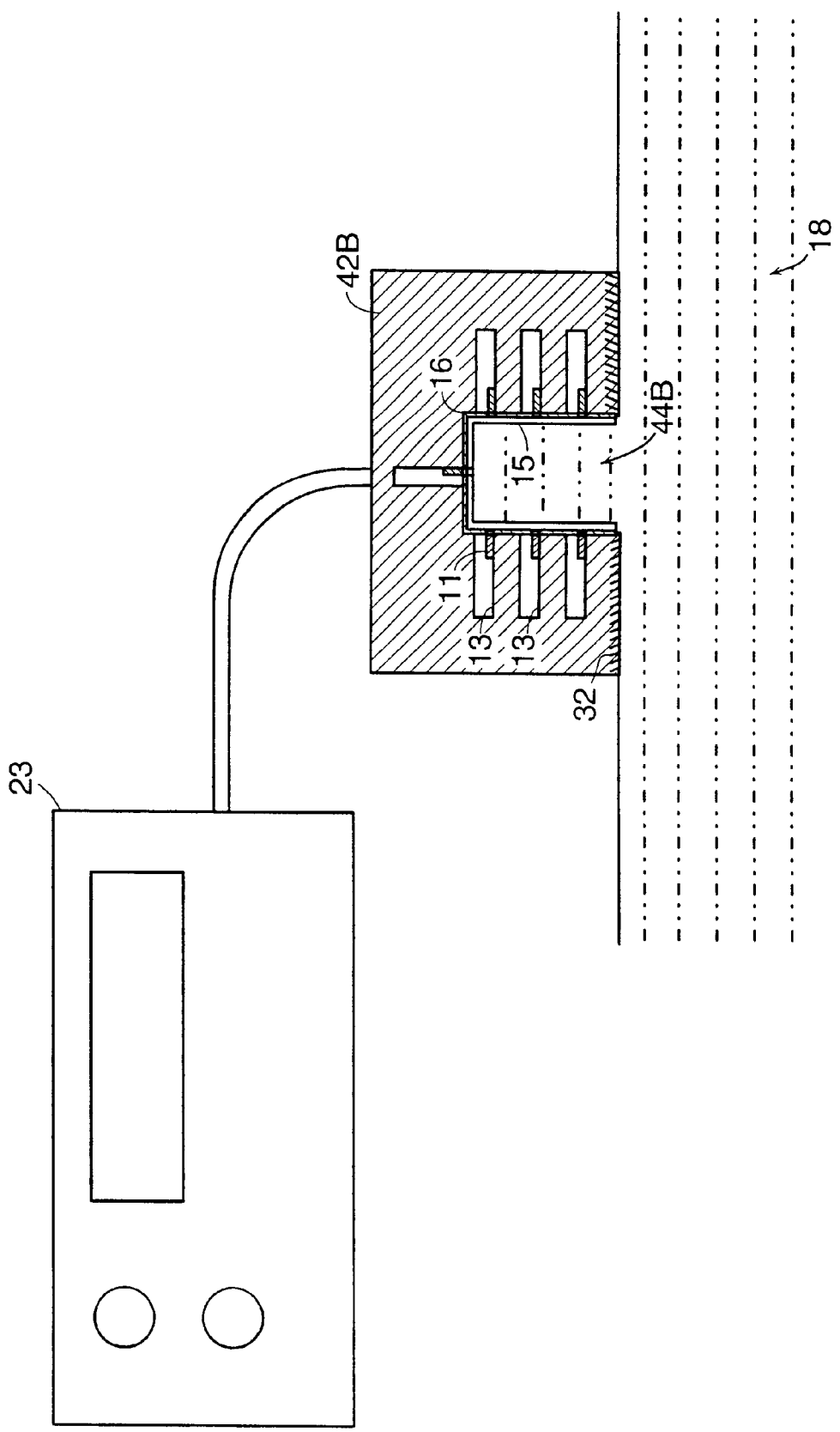
FIGS. 8 and 9 are cutaway, side elevation, semi-schematic representations of a third and fourth species of the third embodiment of the invention.

FIGS. 6–8 illustrate various species of still another embodiment of the invention wherein block 12 is replaced with a block 42 having a recess 44 formed therein. Grooves 13 are formed in a selected pattern around the perimeter of recess 44. In particular, referring to FIG. 6, the block 42A has a semi-cylindrical recess 44A formed therein with grooves 13 having diode bars 11 mounted therein being arranged in a semi-circular pattern around the periphery of recess 44A, each groove 13 and diode bar 11 therein being substantially perpendicular to the circumference of recess 44A (i.e., substantially parallel to a radii) at the point on the circumference where they are located. Part of the media 18 adjacent recess 44A is brought up therein and into contact with transparent surface 15 formed on the inside of the recess. Media may be brought into recess 44A either by pressing block 42A against a relatively soft media 18, for example skin in certain areas, to force the skin into the recess, or a source of vacuum may be provided, either adjacent the bars near the middle of the recess or between such bars, to pull the skin into the recess. Other techniques for forcing skin or other media 18 into the recess 44A may also be employed, either in addition to or instead of one or more of the two techniques mentioned above. Finally, the lower portion of block 42A outside of recess 44A has an angle-dependent reflective coating 32 formed thereon, this surface reflecting some light back into the skin in an area where it may be scattered to recess 44A.

For the embodiment of FIG. 6, the target area for the light energy would be at roughly the foci of the diode bars, which would generally be a point near the bottom center of recess 44A. Any light reflected by the skin prior to reaching such a target area would typically be reflected back into the recess and ultimately returned to the target resulting in a very high illumination increase ratio (f) for this embodiment.

FIG. 7 illustrates an embodiment which differs from that of FIG. 6 in that the recess 44A in block 42A, instead of merely having a thin transparent layer 15, has a transparent block or lens 40 positioned therein with a narrow rectangular recess 48 formed in cylindrical lens 40. Grooves 13 and the diode bars 11 mounted therein are at a slightly greater angle so as to have a focus near the upper middle of recess 48. The embodiment of FIG. 7 is particularly adapted for hair removal applications where a fold of skin having a single hair follicle in the plane of the Figure (there may be several hair follicles in the recess 48 along the length of the recess) is in recess 48 at a given time. Vacuum would normally be required to draw such a fold of skin into recess 48. As for the embodiment of FIG. 6, this embodiment results in a high concentration of light, including light reflected from reflecting surface 16 reaching the target point in recess 48. This effect is further enhanced by providing a highly reflective coating 49 on the bottom surface of cylindrical lens 40 which prevents light from exiting the lens into medium 18. Thus, substantially 100 percent of the light produced by diode bars 11 for this embodiment of the invention is applied to the target area, with virtually no energy being lost to scattering.

FIG. 8 is similar to FIG. 6 except that recess 44B in block 42B has a rectangular cross-section rather than a semicircular cross-section, and grooves 13 are perpendicular to the walls of recess 44B at the points where they are located. While this embodiment does not result in a focusing of the light at a single point as for the embodiments of FIGS. 6 and 7, it does result in a high concentration of light energy in recess 44B which is applied to medium moved into the recess by pressure, vacuum, or other suitable means.

Figure 9:
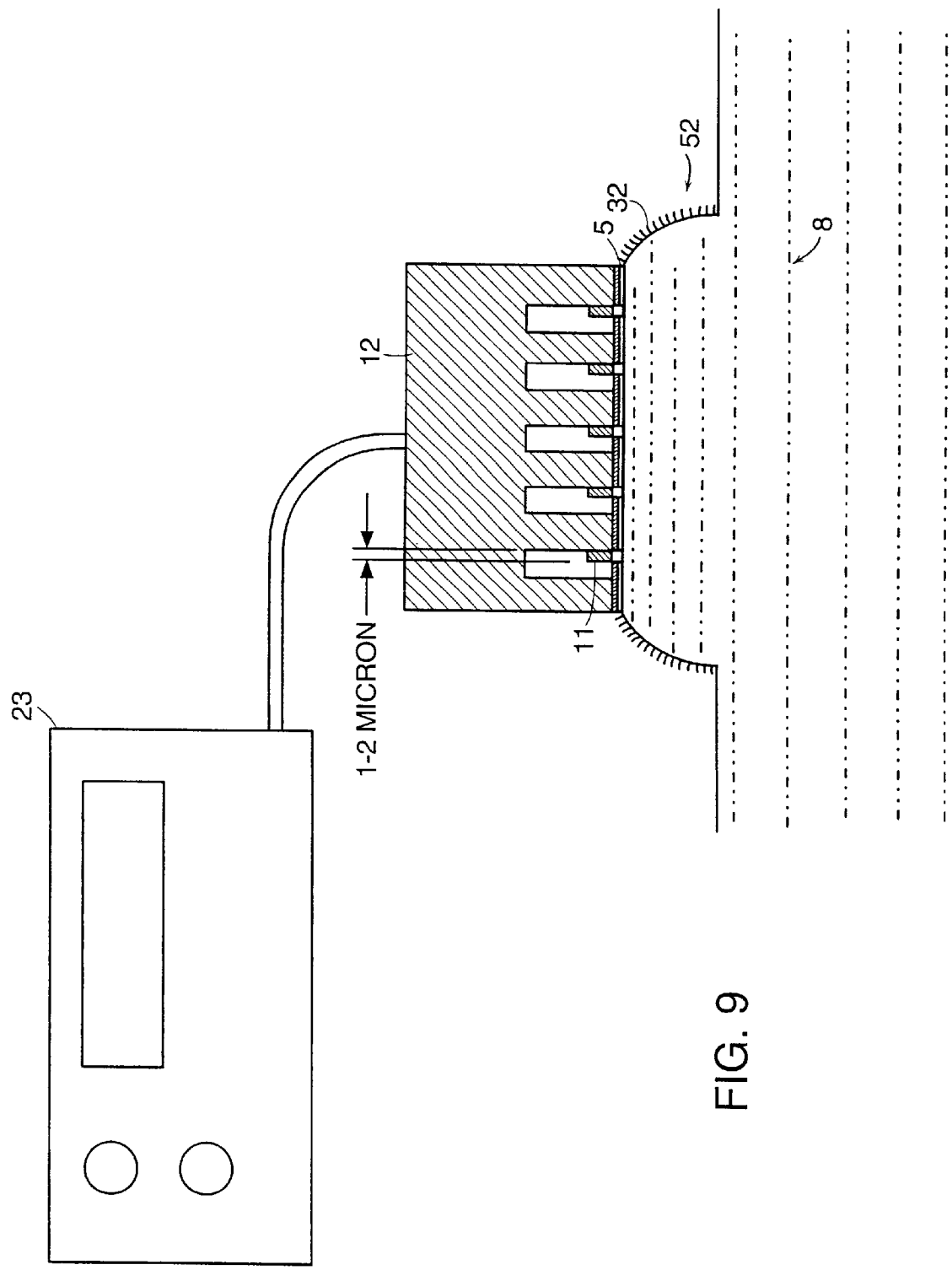

The embodiment of FIG. 9 is similar to that of FIG. 1 except that rather than there being extended portions for layers 15 and 16, there are flexible extensions 52 on each end of the block, which extensions have an angle-dependent reflective coating 32 formed thereon. Vacuum may be used to draw part of medium 18 into the area under block 12 and extensions 52 to provide enhanced radiation of a target area in this region or thereunder. The side sections 52 with angle-dependent reflective coating are more effective in directing light energy in the (d) region (FIG. 10B) into the target area than are the flanges of FIG. 1.

While not specifically mentioned above, the embodiments of FIGS. 6–9 can also utilize the cooling technique of FIG. 1 wherein block 12 and/or block 42 is utilized both to cool diode bars 11 and to cool the surface of the skin or other media 18. The embodiment of FIG. 7 is not as effective for achieving this objective as some of the other embodiments.

Figure 12:
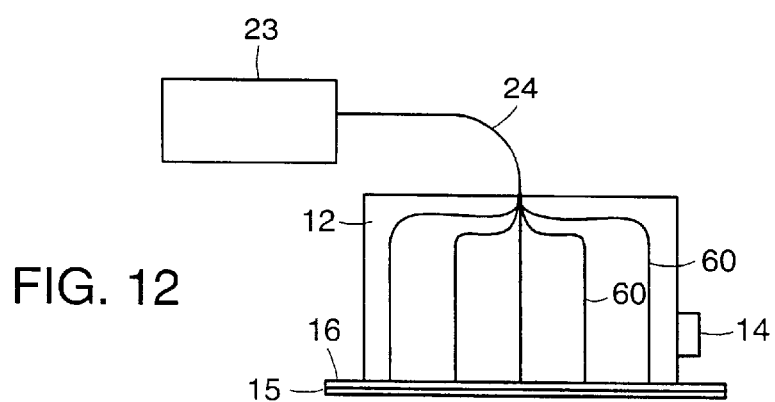
FIG. 12 is a cutaway, side elevation, semi-schematic representation of a fourth embodiment of the invention.

While for the embodiments described above, diode bars have been mounted in block 12 of head 10, in some applications other light emitters, for example filament lamps such as halogen lamps, could be suitably mounted in block 12 in place of the diode bars. Many of the advantages of this invention could also be achieved if a light pipe receiving light from a laser or other light emitting source is substituted for each diode bar 11 for the various embodiments. For example, FIG. 12 shows a head 10' which differs from that shown in FIG. 1 in that light from a laser or other light energy emitter of suitable power and wavelength is passed through a light pipe in lines 24 to a network of light pipes 60 in block 12, there being a plurality of light pipes 60 behind each light pipe shown to provide substantially the same light emission pattern as for the plurality of emitters 11A of each diode bar 11. The minimum aperture size D to achieve a selected amplification (f) from retroreflection is also applicable to substantially any laser or other light energy emitting head used on a scattering medium, including those shown in various prior patents and applications including U.S. Pat. Nos. 5,595,568; 5,735,844; 5,824,023, and application Ser. No. 09/078055, FIG. 4 of which, for example, shows a head which may be used in practicing the teachings of this invention, but which differs from FIG. 12 in that the light pipes are angled to focus the light energy. Where light pipes are utilized, transparent layer or element may not be required, and reflective coating 16 can be applied directly to the bottom surface of block 12, with openings in the coating being provided under each light pipe.

Further, transparent layer 15 is preferably spaced by at least several micron, for example 50–100 microns, from the diode bars to assure against shorting of the laser bars, and this space may be filled with air or other gas, or with a liquid or solid insulating material which is transparent at least in the areas under the openings or slits in the reflective layer 16. For this embodiment, the spacing may be such that cooling of the medium from block 12 is no longer possible.

An invention has thus been disclosed, including a number of embodiments and various species of each embodiment, which provides a simpler cooling mechanism for certain embodiments for the surface of a medium undergoing a laser or other optical energy procedure and which also provides more optimum, and in some cases substantially optimum, use of light energy produced by diode laser bars, or other optical energy source, even when the light is being delivered to a highly scattering medium, by designing the device to provide an adequate input aperture and suitable mechanisms for retroreflecting such light. Further, while a number of embodiments and species thereof have been disclosed, it is apparent that these are being provided for purposes of illustration only and that other similar or equivalent mechanisms might also be employed. Thus, while the invention has been particularly shown and described above with reference to preferred embodiments and species, the foregoing and other changes in form and detail may be made therein by one skilled in the art without departing from the spirit and scope of the invention, which is to be defined only by the appended claims.

What is claimed is:

1. A head for applying optical energy to a selected depth in a scattering medium including:
    a thermally conductive mount having an energy emitting surface, and at least one channel therethrough;
    at least one optical energy emitting element mounted in said mount and in proximity to said energy emitting surface, each said element being in thermal contact with said mount and oriented to direct optical energy through said surface;
    a transparent layer over said surface and in thermal contact therewith, said layer configured to be in contact with said outer layer of the medium, and having good thermal transfer properties; and
    a fluid to flow through the at least one channel to cool said mount, said mount when cooled sinking heat both from said at least one element and from said transparent layer.

2. The head of claim 1, further comprising a thermoelectric component to cool said mount.

3. The head of claim 1, wherein the fluid is a liquid.

4. The head of claim 3, wherein the liquid is water.

5. The head of claim 1, wherein the fluid is a gas.

6. The head of claim 1, wherein the transparent layer is made of sapphire.

7. The head of claim 1, further comprising a concentrator coupled to the mount, the concentrator configured to redirect at least a portion of the optical energy.

8. The head of claim 1, wherein the at least one optical energy emitting element is selected from the group consisting of a laser and a lamp.

9. The head of claim 1, further comprising a reflecting layer on said energy emitting surface, said reflecting layer having at least one opening formed therein through which light energy may be applied to said medium, each of said at least one opening corresponding to one of said at least one element, wherein said reflecting layer has a larger footprint than said energy emitting surface.

10. A head for applying optical energy to a selected depth in a scattering medium having an outer surface including:
    a thermally conductive mount having an energy emitting surface;
    at least one optical energy emitting element mounted in said mount and in proximity to said energy emitting surface, each said element being in thermal contact with said mount and oriented to direct optical energy through said surface;
    a cylindrical lens coupled to said mount to transmit the optical energy, the cylindrical lens in thermal contact with said mount and configured to be in contact with said outer surface; and
    a cooling mechanism for said mount, said mount when cooled sinking heat both from said at least one element and from said cylindrical lens.

11. The head of claim 10, wherein the cylindrical lens collimates the optical energy.

12. The head of claim 10, wherein the cylindrical lens converges the optical energy.

13. A head for applying optical energy to a selected depth in a scattering medium including:
    a thermally conductive mount having an energy emitting surface;
    at least one optical energy emitting element mounted in said mount and in proximity to said energy emitting surface, each said element being in thermal contact with said mount and oriented to direct optical energy through said surface;
    at least one side wall having a reflective surface, the side wall coupled to the mount such that the reflective surface redirects at least a portion of the optical energy; and
    a cooling mechanism thermally coupled to said mount.

14. The head of claim 13, further comprising an angle-dependent reflective coating disposed on said reflective surface.

15. The head of claim 13, wherein the side wall is configured to concentrate the optical energy.

16. The head of claim 13, wherein the side wall is configured to expand the optical energy.

17. The head of claim 13, wherein the side wall is configured so that said reflective surface is normal to said energy emitting surface.

18. The head of claim 13, wherein the sidewall is formed on a slab, and the slab is in thermal contact with the mount.

19. The head of claim 18, wherein said slab is formed of a material having good heat transfer properties.

20. The head of claim 18, further comprising a cooling mechanism thermally coupled to said slab.

* * * * *